United States Patent [19]

Schick et al.

[11] 4,145,406

[45] Mar. 20, 1979

[54] SPECIFIC BINDING - ADSORBENT ASSAY METHOD AND TEST MEANS

[75] Inventors: Lloyd A. Schick; Stephen K. Carpenter, both of Elkhart, Ind.

[73] Assignee: Miles Laboratories, Inc., Elkhart, Ind.

[21] Appl. No.: 786,207

[22] Filed: Apr. 11, 1977

[51] Int. Cl.² ............................................. G01N 33/16
[52] U.S. Cl. ...................................... 424/1; 23/230 B; 424/12
[58] Field of Search ...................... 424/1, 12; 23/230 B

[56] References Cited

U.S. PATENT DOCUMENTS 4,041,146  8/1977  Giaever .................................... 424/1

OTHER PUBLICATIONS

Selhub et al., Febs Letters, vol. 44, No. 1, Aug., 1974, pp. 71-74.
Chidlow et al., Biochem. J., vol. 117, 1970, pp. 49-55.
Peterson et al., Journal of the American Chemical Society, vol. 78, No. 4, Feb. 20, 1956, pp. 751-755.

*Primary Examiner*—Benjamin R. Padgett
*Assistant Examiner*—Christine M. Nucker

*Attorney, Agent, or Firm*—Andrew L. Klawitter

[57] ABSTRACT

A method and test means for determining a specific binding substance, such as an antigen or hapten, in a liquid sample wherein a solid, nonspecific adsorbent is contacted, preferably in sequence, with the sample and a labeled form of a binding partner for the substance to be determined, such as a labeled antibody. The amount of label which becomes associated with the adsorbent by binding of the labeled binding partner to the adsorbed substance to be determined, i.e., in a sandwich fashion, is a function of the amount of the substance to be determined in the liquid sample. Preferably, the adsorbent is an ion exchange material, and the assay steps are carried out under pH conditions between the isoelectric points (pI values) of the substance to be determined and the labeled binding partner. The method and test means are particularly suited for the detection of hepatitis B surface ($HB_s$) antigen, especially where the label is a radioactive material and a column format is employed. The resultant radioimmunoadsorbent (RI-Ad TM) assay and test means for $HB_s$ antigen offers significant manufacturing and user advantages over the prior art methods and test means.

61 Claims, 3 Drawing Figures

SPECIFIC BINDING - ADSORBENT ASSAY METHOD AND TEST MEANS

BACKGROUND OF THE INVENTION

1. Field of the Invention

This invention relates to methods and means for determining a substance in a liquid based on its affinity for a specific binding partner. In one aspect, therefore, the present invention relates to binding assays of the immunological type for determining antigens and haptens or their antibodies. In a preferred embodiment, the present invention relates to radioimmunoassay (RIA) methods and means for detecting hepatitis B surface ($HB_s$) antigen in serum and plasma samples.

There is an ever increasing interest in improving specific binding assay techniques and test means. Classical RIA techniques involve competition between sample antigen and radiolabeled antigen for binding with a specific antibody. The amount of radioactivity which becomes associated with the antibody is a function of sample antigen concentration and can be determined by precipitating, and thereafter separating, the radioactive antigen-antibody complex, or more conveniently, by using an insoluble form of antibody such as antibody coupled to solid particles or matrices. Recently, several alternative labeling materials have been reported for replacement of radioisotopes, including enzymes, coenzymes, enzyme substrates, fluorescent molecules, molecules capable of participating in light producing reactions, and enzyme modulators.

There is a particular need for a more advantageous specific binding assay technique for detecting hepatitis B surface ($HB_s$) antigen in samples of serum or plasma. It is well accepted that a patient can contract hepatitis after receiving a transfusion of blood containing $HB_s$ antigen. Until recently, a wide variety of techniques were used routinely by hospital laboratories and blood banks to detect $HB_s$ antigen in blood drawn for transfusion purposes. Such techniques included immunodiffusion, complement fixation, counterelectrophoresis, latex agglutination, hemagglutination, and RIA. Recently, it has become a requirement in the United States that blood drawn for transfusion be tested for hepatitis by the most sensitive assay techniques available. RIA methods have since become the most widely used for detecting $HB_s$ antigen.

2. Description of the Prior Art

Several specific binding assay techniques have evolved which make use of nonspecific binders or adsorbents. Such specific binding-adsorbent assays fall into two distinct categories:

(1) Use of Adsorbents to Separate Free Label from Bound Label

This category is exemplified by the methods described in U.S. Pat. Nos. 3,414,383; 3,937,799 and 3,938,953 and is usually applied to the detection of small molecules such as hormones, particularly thyroxine. In these methods, competition is initiated in solution between sample ligand and labeled ligand for a specific binding partner, such as a hormone-binding-protein or an antibody. Upon completion of the competitive reaction, free labeled ligand is separated from labeled ligand bound to the binding partner by addition of a nonspecific adsorbent for the free ligand.

(2) Use of Adsorbents to Pre-Extract Sample Ligand

In this method, a nonspecific adsorbent is added to the sample to extract the ligand of interest. The adsorbent is then removed from the sample, adsorbed ligand is eluted off of the adsorbent, and the released ligand is placed in competition with labeled ligand for a specific binding partner. U.S. Pat. Nos. 3,776,698; 3,816,076 and 3,947,564 are representative of this technique. A variation is described in U.S. Pat. No. 3,659,104 for the detection of thyroxine wherein the sample and radiolabeled thyroxine are passed through a column of adsorbent followed by passage of a soluble specific binder, thyroxine binding globulin. The amount of radiolabeled thyroxine eluted from the column is proportional to the amount of thyroxine in the sample.

Nonspecific adsorbents have also been used as sites for competition between sample ligand and labeled ligand, particularly for the determination of hormone uptake values. Application of this technique to the determination of triiodothyronine (T-3) uptake values is described in U.S. Pat. Nos. 3,451,777; 3,710,177 and 3,823,001.

Additional background regarding the use of nonspecific adsorbents in analytical techniques, and in specific binding assays in particular, is afforded by the following: *Principles of Competitive Protein-Binding Assays.* ed. Odell and Daughaday, Chapters IX and XI, J. B. Lippincott Company (1972), and *Clinical Chemistry* 19(2):146–186(1973).

Returning to assay methods specifically for detecting hepatitis, all of the present commercially available RIA methods for detecting $HB_s$ antigen employ a two-site immunoradiometric, or so-called "sandwich", approach. In this technique, the serum sample to be tested is incubated with an insolubilized antibody against $HB_s$ antigen (anti-$HB_s$), such as in the form of anti-$HB_s$ coated on the insides of a test tube or on the surface of plastic beads. A proportion of the insolubilized anti-$HB_s$ becomes bound by sample $HB_s$ antigen if present. The insoluble material is then washed and radiolabeled anti-$HB_s$ added. Following another wash, the amount of radioactivity associated with the insolubilized anti-$HB_s$ is measured as an indication of the presence or absence of $HB_s$ antigen in the sample tested. Exemplary of this RIA approach are the methods described in U.S. Pat. Nos. 3,867,517 and 3,949,064.

While relatively specific and sensitive to $HB_s$ antigen, the prior art "sandwich" RIA approaches leave room for improvement in their manufacture and use. The preparation and quality assurance of the insolubilized anti-$HB_s$ is relatively costly and time consuming. Furthermore, the assay procedure requires two lengthy incubation steps of 30 minutes or more, one for the interaction between sample $HB_s$ antigen and the insolubilized anti-$HB_s$, and the other for interaction with the labeled anti-$HB_s$. Also, the insolubilized anti-$HB_s$ is relatively unstable and requires special shipping and storage conditions.

An additional disadvantage of the prior art RIA approaches is their inability to detect $HB_s$ antigen in the form of its immune complex with anti-$HB_s$ in the sample tested. The nature of the insolubilized anti-$HB_s$ used in the prior art methods is such that it will bind only free $HB_s$ antigen having free antigen determinants and not $HB_s$ antigen-antibody complex. Thus, any danger of post-transfusional hepatitis due to the presence of $HB_s$ immune complex in the transfused blood would go undetected using the available assay methods.

It is therefore an object of the present invention to provide an improved specific binding assay method and test means employing a nonspecific adsorbent for the substance to be determined.

It is a further object to provide a new specific binding assay method and test means for detecting $HB_s$ antigen which alleviates the manufacturing and user drawbacks of the prior art techniques.

It is another object to provide a method and test means for detecting $HB_s$ antigen in the form of its immune complex with anti-$HB_s$.

SUMMARY OF THE INVENTION

The present invention provides a uniquely convenient method and test means for determining a specific binding substance in a liquid sample employing a nonspecific adsorbent and a labeled form of a specific binding partner to the substance to be determined. The assay method, in general, comprises the steps of:

(a) contacting a solid adsorbent with the liquid sample to be tested and with a specific binding partner of the substance to be determined, which binding partner is incorporated with a label and which adsorbent is of a type capable of nonspecifically binding with the substance to be determined, such as an ion exchange material; and (b) determining the amount of the label which either (i) becomes associated with the adsorbent by binding the labeled binding partner with adsorbed substance to be determined or (ii) remains unassociated therefrom, wherein step (a) is performed under conditions favorable to binding between the substance to be determined and the adsorbent, and either the adsorbent is of a type incapable of significantly binding with the labeled binding partner or step (a) is performed under conditions unfavorable to significant binding between the labeled binding partner and the adsorbent.

By nonspecific binding is meant a general physiochemical attraction, such as of an ionic or hydrophobic (van der Waals) type, occurring between the adsorbent and the substance to be determined.

It is preferable that step (a) be accomplished by (i) contacting the sample with the adsorbent, (ii) optionally separating the adsorbent from the unadsorbed portion of the sample, and (iii) thereafter contacting the adsorbent with the labeled binding partner. However, if desired, the adsorbent may be contacted with the sample and the labeled binding partner substantially simultaneously.

Step (b) may be accomplished by separating from the adsorbent substantially all of the labeled binding partner not associated therewith by binding with adsorbed substance to be determined, and measuring the amount of the label either associated with the adsorbent or separated therefrom. This approach is particularly useful where the label is a radioactive material. The present method offers the ability to obtain a concentration effect by contacting the adsorbent with a volume of the sample several times, preferably 2 times, the volume of the adsorbent. The method is applicable to a wide variety of substances and is particularly suited for the detection of $HB_s$ antigen and anti-$HB_s$.

The use of an ion exchange material as the adsorbent provides an assay method particularly suited to the determination of water soluble substances having a net positive or negative electrical charge. The labeled binding partner selected has an isoelectric point (pI value) different from that of the substance to be determined. An ion exchange material and pH conditions can then be selected whereby the adsorbent is capable of nonspecifically binding with the labeled binding partner. The pH conditions are selected to be between the pI value of the substance to be determined and that of the labeled binding partner. Then, if the pI value of the substance to be determined is less than that of the labeled binding partner, an ion exchange material of an anionic type is selected. If the relationship between the pI values is reversed, a cationic type of ion exchange material is selected.

As applied to the detection of hepatitis B surface ($HB_s$) antigen, which has a net negative charge and a pI value of less than about 5, the particularly preferred assay method comprises the steps of:

(a) contacting the sample to be tested with a solid anion exchange material under conditions of pH between 5 and 8;

(b) washing the anion exchange material with a liquid having a pH of between 5 and 8;

(c) contacting the anion exchange material under conditions of pH between 5 and 8 with anti-$HB_s$ incorporated with a label and having a pI value greater than about 8; and (d) determining the amount of the label which either (i) becomes associated with the anion exchange material by binding of the labeled anti-$HB_s$ with adsorbed $HB_s$ antigen or (ii) remains unassociated therefrom.

Preferably the anion exchange material is a diethylaminoethyl-substituted polymer, such as DEAE-cellulose, preferably is in a particulate form, and preferably is contained in a flow-through column.

The present invention also provides a particularly advantageous method for detecting anti-$HB_s$ comprising the steps of:

(a) providing a solid adsorbent having nonspecifically bound thereto $HB_s$ antigen;

(b) contacting the adsorbent with the sample to be tested and with anti-$HB_s$ incorporated with a label; and (c) determining the amount of the label which either (i) becomes associated with the adsorbent by binding of the labeled anti-$HB_s$ to adsorbed $HB_s$ antigen or (ii) remains unadsorbed therefrom.

wherein either the adsorbent is of a type incapable of significantly binding with the labeled anti-$HB_s$ or step (b) is performed under conditions unfavorable to significant binding between the labeled anti-$HB_s$ and the adsorbent.

Also provided by the present invention is a method for detecting $HB_s$ antigen in the form of its immune complex with anti-$HB_s$. Such method comprises the steps of:

(a) combining the sample to be tested with an immunochemical-bond weakening agent, preferably a chaotropic agent such as urea, and with a solid adsorbent of a type capable of and under conditions favorable to nonspecific binding with $HB_s$ antigen, preferably an anion exchange material;

(b) separating said bond weakening agent from the adsorbent; and (c) determining the $HB_s$ antigen bound to the adsorbent, preferably by the method described previously.

DESCRIPTION OF THE PREFERRED EMBODIMENTS

Figure 1:
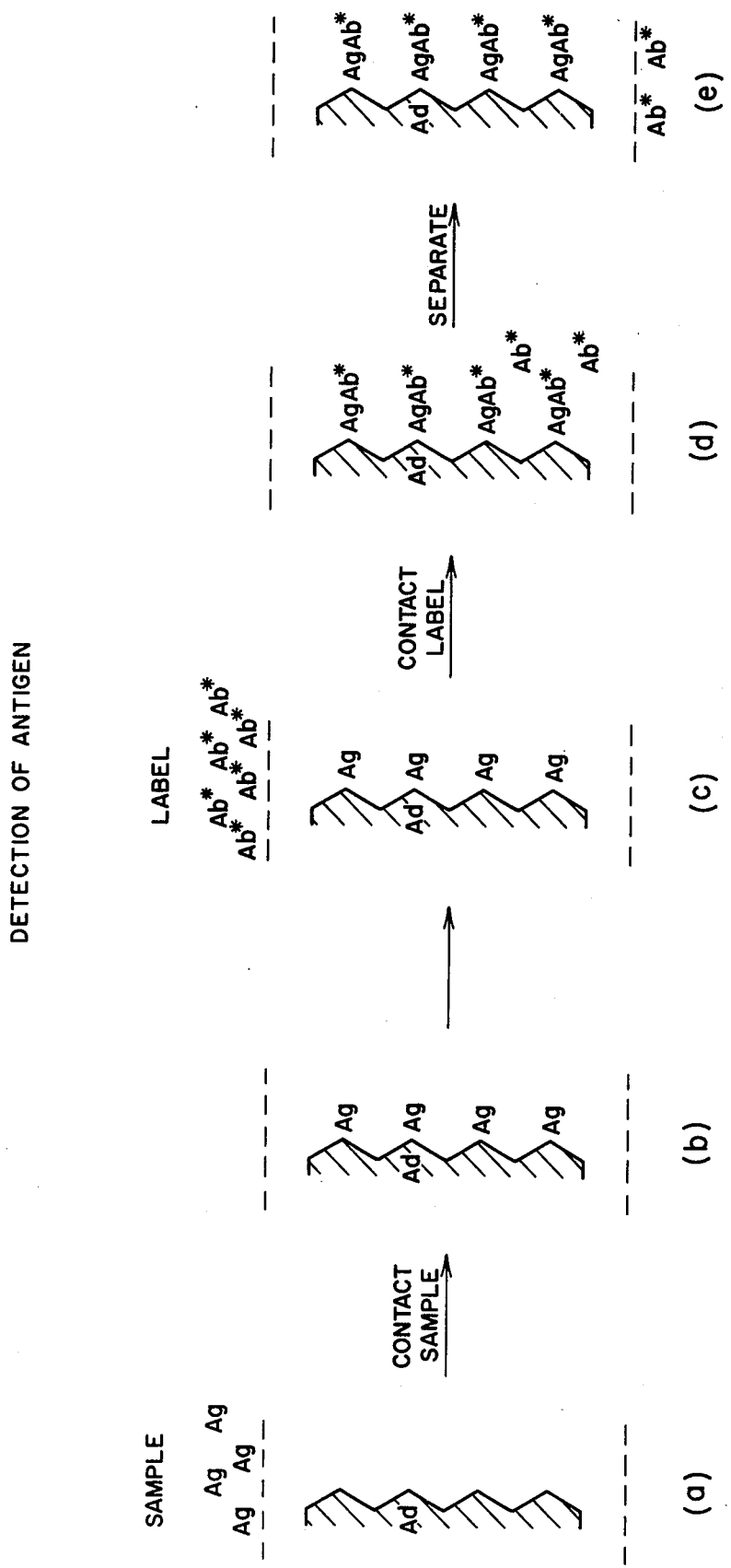
FIG. 1 is a schematic diagram of one form of the present method applied, for illustration purposes, to the detection of an antigen (Ag)

The preferred mechanism by which the present assay method may be accomplished is depicted schematically in FIG. 1 of the drawing. This figure relates, for illustration purposes only, to the detection of an antigen (Ag) using a labeled antibody (Ab*). Any physical form of the adsorbent (Ad) suggested in the diagram is merely illustrative, since the adsorbent may take on a wide variety of forms as will be described more fully hereinafter.

Referring to FIG. 1, a sample suspected of containing an antigen of interest (Ag) is brought into contact with the adsorbent (Ad) as illustrated by steps (a) and (b). A proportion of the antigen present in the sample becomes bound to the adsorbent. Excess labeled antibody (Ab*) is then contacted with the adsorbent, as illustrated by steps (c) and (d), resulting in the association of labeled antibody with the adsorbent by binding with adsorbed antigen. As illustrated by step (e), the excess labeled antibody is separated from the adsorbent with the amount of labeled antibody remaining associated with the adsorbent being a direct function of the amount of antigen present in the sample tested. This method may also be adapted to the detection of antibody by substituting labeled antigen for labeled antibody in steps (c) through (e) and by selecting an appropriate adsorbent and assay conditions.

The adsorbent must have an affinity for nonspecific binding with antigen while having no substantial affinity for antibody, or vice versa where the method is adapted as described in the preceding paragraph for the detection of antibody. Such a situation can be obtained in one way by selecting an adsorbent of a type which by its physical and/or chemical nature is capable of non-specifically binding with the substance to be determined (i.e., antigen in the method depicted in FIG. 1) but which is incapable under any conditions of significantly binding with the labeled binding partner (i.e., labeled antibody in the method depicted in FIG. 1). An example of this situation is the use of an insolubilized lectin, such as Conconavalin A, as the adsorbent in an assay for a carbohydrate-containing antigen, such as a glycoprotein, using a labeled $F_{ab}$ fragment as the specific binding partner. The glycoprotein would be strongly adsorbed by Conconavalin A, whereas the labeled $F_{ab}$ would be unaffected by its presence.

Another way of selecting the necessary binding relationships between the substance to be determined, its labeled binding partner, and the adsorbent is to select an adsorbent which under certain environmental conditions will strongly adsorb the substance to be determined but will not significantly bind with the labeled binding partner. Such environmental conditions affecting the affinity of the adsorbent include pH, ionic strength or salt concentration, and solvent composition. One example of a situation of this type is the use of a hydrophobic material as the adsorbent in an assay for a material containing hydrophobic groups such as $HB_s$ antigen. Under appropriate conditions of ionic strength, hydrophobic materials such as alkyl-substituted agaroses and ω-amino alkyl-substituted agaroses strongly adsorb $HB_s$ antigen but bind only insignificantly with anti-$HB_s$. Another example is the use of a cross-linked dextran gel (e.g., Sephadex ® gel made by Pharmacia AB, Uppsala, Sweden) as the adsorbent in an assay for aromatic haptens or antigens, such as triiodothyronine or tetraiodothyronine (thyroxine). Under appropriate conditions of pH, the aromatic hapten or antigen is strongly adsorbed by the dextran gel whereas subsequently added labeled binding partner (e.g., antibody to triiodothyronine or thyroxine, or thyroxine binding globulin) is not adsorbed significantly.

In addition to ion exchange materials, which will be discussed below, numerous other adsorbent materials may be used in the context of the present invention. Following is a list of some such useful adsorbents.

Adsorbents

Non-ionic cellulose
   e.g., Whatman (Clifton, New Jersey, U.S.A.) types —
      CF-1 ®, long fiber powder
      CF-11 ®, medium fiber powder
      CC-31 ®, microgranular powder
      CC-41 ®, microgranular powder
   e.g., Bio-Rad (Richmond, California, U.S.A.) types —
      Cellex ® N-1, powder
      Cellex ® 410, powder
Silica gel
   e.g., Whatman type — SG 81, loaded paper; or
   Bio-Rad types — Bio-Sil ® A or Bio-Sil ® HA
Hydroxylapatite (Bio-Rad)
Alumina; acid, base, or neutral types (Bio-Rad)
Alumina C-gamma gel (Bio-Rad)
Calcium phosphate
Hydroxypropyl dextran
   e.g., Pharmacia (Piscataway, New Jersey, U.S.A.) type — Sephadex ® LH 20
Dextan (Pharmacia)
Dextran sulfate (Pharmacia)
Alkyl agaroses
   e.g., Pharmacia types — octyl-Sepharose ® CL-4B or phenyl-Sepharose ® CL-4B
   e.g., Miles Research Products (Elkhart, Indiana, U.S.A.) types — ω-amino alkyl agaroses
Lectin-agarose (Miles Research Products)
Poly-L-lysine agarose (Miles Research Products)
Plastics, e.g., polystyrene, polyethylene, and polypropylene It will be recognized by one skilled in the art that various adsorbent/substance to be detected/labeled binding partner combinations may be adapted to the assay method and test means of the present invention.

It is particularly preferred to use an ion exchange material as the adsorbent when the substance to be determined is water soluble and has an isoelectric point (pI value) different from that of a labeled specific binding partner. The difference between the pI values of the substance to be determined and the labeled binding partner usually should be at least 0.5 and preferably is greater than 2.0. The isoelectric point of a substance is the pH at which the substance has no net electrical charge. When in solution, the effective charge of such a substance depends upon the pH of its environment. In a solution having a pH above that of the pI value of a substance, such substance will take on an effective net negative charge. Conversely, such substance will take on an effective net positive charge in a solution having a pH below that of its pI value. The charged substance in solution will have an affinity for an ion exchange material bearing an opposite charge. Thus, a negatively charged substance will be attracted by an anion exchange material and a positively charged substance will be attracted by a cation exchange material. Therefore, in carrying out the present method, the substance to be determined will be adsorbed by the ion exchange material, while the labeled binding partner will not, by selecting an ion exchange material (i) of an anionic type when the pI value of the substance to be determined is less than that of the labeled binding partner, or (ii) of a cationic type when the pI value of the substance to be determined is greater than that of the labeled binding partner; and by performing the assay under conditions of pH between the pI values of the substance to be determined and the labeled binding partner. Following are lists of various ion exchange materials that may be used in accordance with the present invention:

Anion Exchange Materials

Diethylaminoethyl (DEAE) cellulose
  e.g., Whatman types —
    DE-1 ®, floc
    DE-11 ®, powder
    DE-22 ®, fibrous
    DE-23 ®, fibrous
    DE-32 ®, dry, microgranular
    DE-52 ®, wet, microgranular
    DE-81 ®, paper
  e.g., Bio-Rad type — Cellex ® D, fibrous
Diethylaminoethyl (DEAE) agarose
  e.g., Bio-Rad type — DEAE Biogel ® A
Diethylaminoethyl (DEAE) dextran
  e.g., Pharmacia type — DEAE Sephadex ®, bead
Aminohexyl-Sepharose ® 4B (Pharmacia)
Ecteola cellulose
  e.g., Whatman types — 'ET-11 ®, powder
    ET-41 ®, powder (high purity)
    ET-81 ®, paper
  e.g., Bio-Rad type — Cellex ® E, fibrous
Triethylaminoethyl (TEAE) cellulose
  e.g., Bio-Rad type — Cellex ® T, fibrous
Diethyl-(2-hydroxypropyl)-amino (QAE) cellulose
  e.g., Bio-Rad type — Cellex ® QAE, fibrous
Diethyl-(2-hydroxypropyl)-amino (QAE) dextran
  e.g., Pharmacia type — QAE-Sephadex ®
Benzoylated diethylaminoethyl cellulose
  e.g., Bio-Rad type — Cellex ® BD, fibrous Cation Exchange Materials Cellulose phosphate
  e.g., Whatman types —
    P-1 ®, floc
    P-11 ®, powder
    P-41 ®, powder (high purity)
    P-81 ®, paper
Carboxymethyl cellulose
  e.g., Whatman types —
    CM-1 ®, floc
    CM-11 ®, powder
    CM-22 ®, fibrous
    CM-23 ®, fibrous
    CM-32 ®, dry, microgranular
    CM-52 ®, wet, microgranular
    CM-82 ®, paper
  e.g., Bio-Rad type — Cellex ® CM, fibrous
Carboxymethyl dextran
  e.g., Pharmacia type — CM-Sephadex ®
Phosphoryl cellulose
  e.g., Bio-Rad type — Cellex ® P, fibrous
Carboxymethyl agarose
  e.g., Bio-Rad type — CM Biogel ® A
  e.g., Pharmacia type — CH-Sepharose ® 4B
Sulphopropyl dextran
  e.g., Pharmacia type — SP-Sephadex ®

[For further information on the use of ion exchange materials as adsorbents see *J. Amer. Chem. Soc.* 78:756–763(1956) and *J. Infect. Dis.* 129:371–375(1974).]

A table illustrating various pairs of specific binding substances having different pI values follows:

| First Substance of Pair | pI | Second Substance of Pair | pI |
|---|---|---|---|
| HB$_s$ antigen | 3.5–5 | Anti-HB$_s$ | 7–8 |
| Thyroxine-binding-globulin (TBG) | 4.5 | Anti-TBG | 7–8 |
| Albumin | 4.5 | Anti-albumin | 7–8 |
| IgG | 7–8 | Carbamylated anti-IgG | 5 |
| Thyroid-stimulating-hormone (TSH) | 9.5 | Carbamylated anti-TSH | 5 |
| Ferritin | 5.4 | Anti-ferritin | 7–8 |
| Alkaline phosphatase (AP) | 4.3–5 | Anti-AP | 7–8 |
| Fibrinogen | 5.5 | Anti-fibrinogen | 7–8 |
| Follicle-stimulating-hormone (FSH) | 3.0 | Anti-FSH | 7–8 |
| Insulin | 5.6 | Anti-insulin | 7–8 |
| Lysozyme | 10–11 | Anti-lysozyme | 7–8 |
| Plasminogen | 6.5–8 | Carbamylated anti-plasminogen | 5 |
| Prothrombin | 4.6 | Anti-prothrombin | 7–8 |
| Thyroglobulin | 4.5 | Anti-thyroglobulin | 7–8 |
| Transcobalamin | 6.2 | Anti-transcobalamin | 7–8 |
| Thyroxine | 7.5 | Thyroxine-binding-globulin (TBG) or | 4.5 |
|  |  | Anti-thyroxine | 7–8 |
| Luteinizing-hormone (LH) | 5 | Anti-LH | 7–8 |

The present method is applicable to the detection of either or both of the above listed first and second substances by selection of an anionic or cationic exchange material according to the guidelines given herein.

The adsorbent may take any physical form which allows interaction between its adsorption sites and the corresponding nonspecific binding sites on the substance to be determined and which allows further interaction of the adsorbed substance to be determined with the labeled binding partner. The adsorbent can take a wide variety of shapes of solid insoluble materials, usually of a polymeric nature. A particulate form, such as that of powders, beads, filaments and crystals, is preferred because of the relatively large surface area available; however, sponges, sheets, strips, pads, and other integral matrices and lattices may also be used even to the point of carrying out the assay in a vessel, such as a test tube or plate well, constructed in whole or in part of the adsorbent material. In addition to its large surface area, a particulate form is conveniently dispensable into a test vessel or reaction chamber and is readily useable in a column, flow-through format.

Figure 2:
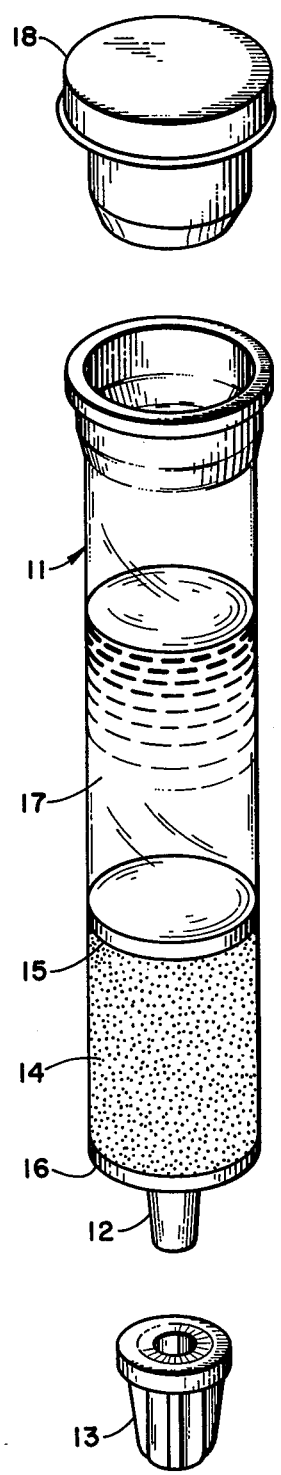
FIG. 2 is an exploded perspective view of a column test device which may be comprised in test means for carrying out the present method.

An illustration of a column test device preferred for use in the present method is provided in FIG. 2 of the drawing. The depicted column test device comprises a cylindrical tubular body 11 terminating at one end in a tapered tip portion 12. The body 11 is formed of polypropylene or other suitable material and is provided with valve means, such as a friction fit bottom cap 13, which fits over and removably closes tip portion 12. A bed 14 of the adsorbent, such as an ion exchange material in particulate form, is retained between two porous polyethylene discs 15 and 16 in the lower portion of body 11. A reservoir 17 is provided in body 11 above the disc 15. In FIG. 2 a quantity of liquid buffer is shown disposed within the reservoir 17. A removable top cap 18 is provided for sealing the upper end of body 11 to provide an integral closed device for shipping and storage. The packed bed volume is preferably between 0.25 and 2.0 ml. The body 11 is preferably between 5 and 30 mm in diameter and between 50 and 150 mm in height.

With reference to the present method in its broadest aspects, it is preferred that the adsorbent be contacted with the test sample, separated from the unadsorbed portions of the sample, and then contacted with labeled binding partner. Separation of the adsorbent from unadsorbed portions of the sample assures removal of possible interferants from the sample which, if allowed to remain during the application of the labeled binding partner, might affect reproducibility by promoting nonspecific binding of the labeled material or otherwise. This separation is conveniently accomplished by washing the adsorbent under conditions favorable to adsorption of the substance to be determined. For example, following the method employing an ion exchange material as the adsorbent, the washing liquid may be a buffer having a pH between the pI values of the substance to be determined and the labeled binding partner.

The determination of the amount of the label which either (i) becomes associated with the adsorbent by binding of the labeled binding partner with adsorbed substance to be determined or (ii) remains unassociated therefrom may be accomplished in either of two ways. First, where the binding of the labeled binding partner with the adsorbed substance to be determined measurably alters some determinable characteristic of the label, the extent of alteration of such characteristic may be determined directly in the mixture formed upon introduction of the labeled binding partner to the adsorbent, much in the manner associated with "homogeneous" binding assays, with no need to separate "bound" label from "free" label. Such a situation could arise where the label used is an enzyme or coenzyme, or other material having a monitorable characteristic, and the binding of the labeled binding partner and the adsorbed substance to be determined would affect, either by inhibition or enhancement, the enzymatic or coenzymatic activity, or other characteristic, of the label.

In the second method, a separation is accomplished between the adsorbent and substantially all of the labeled binding partner not associated therewith by binding with the adsorbed substance to be determined, and the amount or an alterable characteristic of the label is measured either associated with the adsorbent or separated therefrom. This technique is required where the label is unaffected by binding between the labeled binding partner and the adsorbed substance to be determined, but can also be followed where some characteristic of the label is affected. Examples of the former type of label which are particularly useful in the present method are radioactive materials such as $^3H$, $^{131}I$ and $^{125}I$. However, it is contemplated that any of the known labels used in binding assays may be utilized. The separation required by this technique is conveniently accomplished by washing the adsorbent under conditions favorable to adsorption of the substance to be determined and, unless the adsorbent is of a type incapable of significant binding with the labeled binding partner, unfavorable to adsorption of the labeled binding partner. The amount of the label remaining associated with the washed adsorbent or contained in the washings can be related to the presence, or amount, of the substance to be determined in the sample tested by comparison with a negative control, or standard curve, respectively. Other methods can also be used to accomplish the desired separation, including centrifugation and filtration.

The present method is especially useful for the detection of hepatitis B surface ($HB_s$) antigen in liquid samples such as serum or plasma samples. As mentioned previously, various hydrophobic materials can act as adsorbents for $HB_s$ antigen, including certain alkyl-substituted polymers such as ω-aminoalkyl-substituted agaroses. Particularly preferred, however, are ion exchange materials. The pI value for $HB_s$ antigen falls roughly within the range of 3.5 to 5, and for anti-$HB_s$, roughly around 8. The assay conditions are therefore maintained between 5 and 8, and preferably between 6 and 8, and an anion exchange material is used as the adsorbent. Useful anion exchange materials are diethylaminoethyl-substituted polymers, particularly those having a polysaccharide, e.g., cellulose or dextran, backbone. DEAE-cellulose has been found to be a particularly useful $HB_s$ antigen adsorbent. It is contemplated that a cation exchange material such as carboxymethyl cellulose may be used as the adsorbent if the pI value of the labeled anti-$HB_s$ were altered to a value below that of $HB_s$ antigen.

A particularly useful method for detecting $HB_s$ antigen in a serum or plasma sample using an anion exchange material in particulate form and contained in a column involves the steps of:

(a) introducing the sample to a column of an anion exchange material in particulate form equilibrated in a liquid, such as a buffer, having a pH of between 5 and 8, preferably between 6.5 and 7.5;

(b) passing through the column a liquid, such as a buffer, having a pH of between 5 and 8, preferably between 6.5 and 7.5, to remove substantially all $HB_s$ antigen not adsorbed to the anion exchange material;

(c) introducing to the anion exchange material a predetermined volume of a solution of radiolabeled anti-$HB_s$ having a predetermined level of radioactivity;

(d) incubating the solution of radiolabeled anti-$HB_s$ in contact with the anion exchange material for between ½ and 18 hours, preferably between 1 and 3 hours, at a temperature of between 4° and 50° C., preferably between 40° and 50° C.;

(e) passing through the column a liquid, such as a buffer, having a pH of between 5 and 8, preferably between 6.5 and 7.5, to remove substantially all radiolabeled anti-$HB_s$ not associated with the anion exchange material by binding to adsorbed $HB_s$ antigen;

(f) measuring the radioactivity of the anion exchange material or of the eluate from the next previous step; and (g) comparing the radioactivity measured in the next previous step to that measured following the same procedure using a liquid sample containing no significant amount of $HB_s$ antigen in place of the serum or plasma sample.

Examples of buffers referred to in steps (a), (b), and (e) are phosphate buffer, barbital buffer, citrate buffer, tris-(hydroxymethyl)-aminomethane (TRIS) buffer, 4-(2-hydroxyethyl)-1-piperazineethanesulfonic acid (HEPES) buffer, and 1,4-piperazine-bis-(ethanesulfonic acid) (PIPES) buffer.

The particular advantages of the present method for detecting $HB_s$ antigen over the prior art methods include the manufacturing advantages of eliminating the need for insolubilized anti-$HB_s$, which is a significant cost and stability factor in most prior art methods, and the user advantages of a single incubation step, fewer manipulations, storability of adsorbent materials, increased sensitivity, and versatility of detecting $HB_s$ antigen in the form of its immune complex if desired.

In addition to the detection of $HB_s$ antigen, the present method is readily adaptable to the detection of $HB_s$ antigen in the form of its immune complex with anti-$HB_s$ and to the detection of anti-$HB_s$ itself.

The detection of $HB_s$ antigen bound to anti-$HB_s$, i.e., in the form of its immune complex, is carried out by:

(a) combining the sample to be tested, an immunochemical-bond weakening agent, and a solid adsorbent of a type capable of, and under conditions favorable to, nonspecific binding with $HB_s$ antigen;

(b) separating said bond weakening agent from the adsorbent, such as by washing; and (c) determining the $HB_s$ antigen bound to the adsorbent.

By an "immunochemical-bond weakening agent" is meant a substance capable of decreasing the affinity of anti-$HB_s$ for $HB_s$ antigen in the presence of the adsorbent such that at least one antigenic determinant site is made available on the $HB_s$ antigen upon separation of the bond weakening agent and the adsorbent. Such a bond weakening agent may be an acid or an alkali or other materials known for this purpose such as those referred to as chaotropic agents, e.g., urea, guanidine, or thiocyanate. [See *Immunochem.* 1:289–293(1964); *Biochim. Biophys. Acta* 107:593–596(1965); and *Arch. Biochem. Biophys.* 116:82–91(1966).] The combined use of an anion exchange material, preferably DEAE-cellulose, and a urea solution, preferably at a concentration of between 2 and 8 molar, is particularly effective in this method for detecting $HB_s$ antigen immune complex. The amount of $HB_s$ antigen bound to the adsorbent may be determined by any available means but preferably is carried out by adding labeled anti-$HB_s$ and measuring the amount of label that becomes associated with the adsorbent in the manner discussed previously concerning the detection of $HB_s$ antigen.

Anti-$HB_s$ can be determined by following the general method discussed previously, that is, by contacting a test sample with an adsorbent for anti-$HB_s$, thereafter with labeled $HB_s$ antigen and determining the amount of label which either becomes associated with the adsorbent or remains unassociated therefrom. Additionally, the availability of strong adsorbents for $HB_s$ antigen, such as ion exchange materials, can be taken advantage of in the detection of anti-$HB_s$ by following the method of:

(a) providing a solid adsorbent having nonspecifically bound thereto $HB_s$ antigen;

(b) contacting the adsorbent with the sample to be tested and with anti-$HB_s$ incorporated with a label; and (c) determining the amount of the label which either
 (i) becomes associated with the adsorbent by binding of the labeled anti-$HB_s$ to adsorbed $HB_s$ antigen or (ii) remains unadsorbed therefrom, wherein either the adsorbent is of a type incapable of significantly binding with the labeled anti-$HB_s$ or step (b) is performed under conditions unfavorable to significant binding between the labeled anti-$HB_s$ and the adsorbent. This method allows the selection of adsorbent, reaction conditions, i.e., pH, temperature and incubation times, and labeled anti-$HB_s$ to be based on the same criteria as discussed at length above for the detection of $HB_s$ antigen.

In general, the test means of the present invention comprises, usually in a kit or test system form, (a) a solid adsorbent of a type capable of nonspecifically binding with the substance to be determined and (b) a labeled form of a specific binding partner of the substance to be determined. The test means may additionally include a liquid buffer for use in performing one or more of the wash steps preferred in carrying out the assay method. The type of adsorbent, the character, e.g., pH, of the buffer, and the type of label are selected according to the criteria described previously relative to the assay method. Where the test means is designed for the detection of $HB_s$ antigen immune complex, it additionally comprises a solution of the appropriate immunochemical-bond weakening agent.

The adsorbent is preferably arranged in a column format, and in such format, is preferably in a particulate form as discussed previously. The column format not only provides a convenient system for introducing sample and labeled binding partner to the adsorbent, for washing the adsorbent, and for counting radioactivity where the label is a radioactive material, but it also provides a means of concentrating on the adsorbent the substance to be determined from the sample. The column format allows a relatively large volume of sample to be passed through or by the adsorbent, thereby effectively concentrating the substance to be determined relative to a later applied labeled binding partner.

Additionally, the effective concentration of the substance to be determined may be increased by first treating the sample to precipitate the substance to be determined, recovering the precipitate, and redissolving it in a smaller volume of solvent. The resulting solution of the substance to be determined can then be applied to the adsorbent and the assay method completed as described herein. For example, in detecting $HB_s$ antigen, one can add polyethylene glycol to a serum sample to precipitate $HB_s$ antigen, centrifuge or filter, and dissolve the $HB_s$ antigen in a small volume of buffer. The resulting solution will contain an effectively greater concentration of $HB_s$ antigen than was present in the serum sample.

It is contemplated that the present assay method and test means may be applied to the qualitative or quantitative determination of any substance for which there is a natural or synthetic specific binding partner, including peptides, proteins, carbohydrates, glycoproteins, steroids, antigenic particles, and so forth. For example, the following materials may be detected using the present assay method and test means: hormones, such as tetraiodothyronine (thyroxine) and triiodothyronine; enzymes, such as lactic dehydrogenase and alkaline phosphatase; therapeutic agents, such as gentamicin and diphenylhydantoin, virus particles, such as $HB_s$ antigen and bacteriophages; whole bacterial cells; and nucleic acids, such as deoxyribonucleic acid (DNA) and ribonucleic acid (RNA), to name just a few. The present invention is particularly suited to the detection of antigens and haptens, and antibodies thereto, particularly $HB_s$ antigen and anti-$HB_s$. Various liquid specimens may be analyzed according to the present invention, particularly physiological or biological fluids such as serum, plasma, urine, saliva, and amniotic, cerebral and spinal fluids.

The present invention will now be illustrated, but is not intended to be limited, by the following examples.

EXAMPLE 1

Radioimmunoadsorbent Assay (RI-Ad TM) for Hepatitis B Surface Antigen

This Example describes an assay procedure for the detection of $HB_s$ antigen using an anion exchange material as nonspecific adsorbent. The accuracy of the RI-Ad procedure was assessed against the United States Bureau of Biologics (BOB) Reference Panel No. 3. The sensitivity of the RI-Ad procedure was determined relative to the Ausria® II radioimmunoassay test kit marketed by Abbott Laboratories, North Chicago, Illinois U.S.A.

A. Preparation of Assay Columns

The columns comprised 0.5 milliliter (ml) of settled anion exchange resin, DEAE-cellulose type DE-52, Whatman Inc., Clifton, New Jersey U.S.A., held in a 9.5 × 75 millimeter (mm) polyethylene column between two porous polyethylene discs. The columns were fitted with top and bottom caps after equilibration with a volume of 0.02M sodium monobasic phosphate: sodium dibasic phosphate buffer (herein referred to as "phosphate" buffer) at pH 6.8, the buffer volume being sufficient to saturate the resin bed and provide about a 1 ml buffer in the reservoir above the bed. The geometry of the column was selected to facilitate the measurement of radiation emitted from the resin bed with conventional gamma counting instrumentation, such as the Gammacord® instrument marketed by the Ames Company Division of Miles Laboratories, Inc., Elkhart, Indiana U.S.A. The general configuration of the complete test column was similar to that depicted in FIG. 2 of the drawing.

B. Assay Procedure

1. The top cap was removed and the column placed in a drain rack.

2. A 200 microliter (μl) volume of the serum or plasma test sample, or a negative control sample, was added to the buffer in the reservoir above the DEAE-cellulose resin bed. The column was swirled to mix the sample and buffer and was then drained by removal of the bottom cap.

3. The resin bed was washed with two consecutive additions of 4 ml of 0.02M phosphate buffer (pH 6.8).

4. When the column had drained completely, a 200 μl volume of $^{125}$I-anti-$HB_s$ [specific activity of labeled anti-$HB_s$ = 14–20 microcurie/microgram (μCi/μg); total activity = approx. 50,000 counts per minute (cpm)] was added to the top of the resin bed and allowed to soak into the resin after which the bottom cap was replaced. [Anti-$HB_s$ used had been raised against $HB_s$ antigen, purified by the method of Ling and Overby, J. Immunol. 109:834(1972), and labeled by the chloramine T method of Hunter and Greenwood, Nature 194:495(1962)].

5. The column was then incubated either (i) for 2 hours at 45° C. (the "2 hour/45° C." assay) or (ii) overnight at room temperature, 22° C. (the "overnight/RT" assay).

6. The bottom cap was then removed and the resin bed was washed with two consecutive additions of 4 ml of 0.02M phosphate buffer (pH 6.8).

7. When the column had drained completely, the bottom cap was replaced and the column placed in the well of a gamma counting instrument, such as the aforementioned Gammacord instrument, and its radioactivity counted. (In an alternative procedure the washings from previous step 6 are collected and their aggregate radioactivity measured.)

8. A positive sample was determined as one which yielded a level of radioactivity associated with the resin bed greater than (or which yielded a level of radioactivity in the washings less than) a cut-off value calculated as the average cpm of gamma radiation yielded by the resin beds (cpm bound) (or contained in the washings, where the alternative procedure is followed) of at least seven replicates of a negative control plus (or minus, where the alternative procedure is followed) four standard deviations. An example of a calculation of a cut-off value where the resin bed cpm bound is measured is as follows:

Seven replicate samples of a negative control are run separately through the assay procedure and the counts per minute (cpm) of gamma radiation associated with the resin bed (cpm bound) for each run is recorded.

| Replicate No. | Cpm bound |
| --- | --- |
| 1 | 1459 |
| 2 | 1488 |
| 3 | 1398 |
| 4 | 1444 |
| 5 | 1543 |
| 6 | 1487 |
| 7 | 1387 |
| total | 10206 |
| average | 1458 |
| standard deviation | ±54 |
| cut-off | 1458 + (4 × 54) = 1678 |

Therefore, any sample tested which would give a cpm bound greater than 1678 would be considered as positive for $HB_s$ antigen.

C. Accuracy — Performance with BOB Panel

Each BOB panel sample was assayed by both the 2 hour/45° C. procedure and the overnight/RT procedure. The results appear in Table 1. In the table, the BOB codes stand for the following:

| BOB Code Letter | Meaning |
| --- | --- |
| A | contains relatively high level of $HB_s$ antigen detectable by all current methods |
| B | contains a lesser level of $HB_s$ antigen detectable by counter electrophoresis, reversed passive latex agglutination, reversed passive hemagglutination, and radioimmunoassay |
| C | contains even lesser level of $HB_s$ antigen detectable consistently only by reversed passive hemagglutination |

| BOB Code Letter | Meaning |
|---|---|
| | and radioimmunoassay |
| (C) | contains low level of $HB_s$ antigen occassionally detectable by radioimmunoassay |
| D | contains very low level of $HB_s$ antigen not detectable by any current method |
| N | a true negative for $HB_s$ antigen |

The calculations of the cut-off values for the 2 hour/45° C. and the overnight/RT procedures were as follows:

| Cut-Off Value Calculations | 2 hours/45° C. | overnight/RT |
|---|---|---|
| average cpm bound for negative control replicates | 3374 | 5404 |
| standard deviation (S.D.) | ±117 | ±123 |
| percent coefficient of variation (% C.V.) | 3.46 | 2.27 |
| cut-off value (cpm) | 3842 | 5896 |

Table 1

| Sample Number | BOB Code | Cpm (2 hours/45° C) sample | sample-CO* | Cpm (overnight/RT) sample | sample-CO* |
|---|---|---|---|---|---|
| 302 | D | 3403 | Neg | 4960 | Neg |
| 303 | N | 3481 | Neg | 4478 | Neg |
| 304 | C | 8160 | +4318 | 12100 | +6204 |
| 306 | A | 22377 | +18535 | 24197 | +18301 |
| 311 | N | 3680 | Neg | 4202 | Neg |
| 312 | A | 21122 | +17280 | 24095 | +18199 |
| 315 | (C) | 3411 | Neg | 5853 | Neg |
| 317 | N | 3325 | Neg | 4970 | Neg |
| 318 | C | 21570 | +17738 | 25880 | +19984 |
| 319 | B | 18378 | +14536 | 22731 | +16835 |
| 320 | B | 24730 | +20888 | 30057 | +24163 |
| 323 | C | 5569 | +1727 | 7721 | +1825 |
| 326 | C | 18589 | +14747 | 21773 | +15877 |
| 327 | B | 2776 | +23934 | 32403 | +26507 |
| 330 | A | 21360 | +17518 | 25155 | +19259 |
| 331 | N | 3182 | Neg | 4838 | Neg |
| 332 | C | 9993 | +6151 | 16709 | +10813 |
| 333 | C | 9891 | +6049 | 13684 | +7788 |
| 336 | B | 21471 | +17629 | 29233 | +23337 |
| 337 | C | 19724 | +15882 | 23139 | +17243 |
| 338 | C | 4793 | +951 | 6672 | +776 |
| 343 | (C) | 4606 | +754 | 6236 | +1340 |
| 344 | C | 4388 | +546 | 6939 | +1043 |
| 349 | D | 3625 | Neg | 6446 | +550 |
| 350 | B | 22265 | +18423 | 28162 | +22266 |

*sample cpm bound minus cut-off (CO) value

The RI-Ad procedure using both incubation conditions correctly identified every BOB panel member having a code of A, B, or C. There were no false positives as every N coded BOB panel member yielded a negative result. Additionally, BOB panel member number 343 coded as (C) was picked up as a positive by the RI-Ad procedure under both incubation conditions and even one D coded panel member, number 349, was picked up as positive by the overnight/RT RI-Ad procedure.

D. Sensitivity — Comparison with Ausria II

Three positive BOB panel members (sample numbers 312, 326 and 336) and one negative member (sample number 317) were selected. Dilutions of each were prepared between 1:50 and 1:64,000. Selected dilutions were assayed using the RI-Ad procedure, under both incubation conditions, i.e., 2 hours/45° C. (2 hr) and overnight/RT (ON), and using Ausria II kits, Abbott Laboratories, North Chicago, Illinois U.S.A., following the procedure given in the product insert (the insert specifies that a "P/N Ratio" of 2.1 or more represents a positive sample result). The results appear in Table 2. The positive cut-off value calculations for the RI-Ad procedures are given at the bottom of the table. "N.C." represents the average cpm bound for the negative control replicates; "S.D.", standard deviation; and "%C.V.", percent coefficient of variation.

The RI-Ad procedure was shown to be at least as sensitive under both incubation conditions as the Ausria II procedure, and in certain circumstances showed greater sensitivity. For example, the 1:64,000 dilution of panel member number 312 (Code A) was determined as positive using the 2 hour RI-Ad procedure but negative using Ausria II.

Table 2

| | | BOB #312 (A) | | | BOB #326 (C) | | | BOB #336 (B) | | | BOB #317 (N) | |
|---|---|---|---|---|---|---|---|---|---|---|---|---|
| | | RI-Ad, cpm | | Ausria II | RI-Ad, cpm | | Ausria II | RI-Ad cpm | | Ausria II | RI-Ad, cpm | |
| Dilution | | 2 hr | O.N. | P/N Ratio | 2 hr | O.N. | P/N Ratio | 2 hr | O.N. | P/N Ratio | 2 hr | O.N. |
| 1/50 | | — | — | — | 5954 | 8235 | 8.3 | — | — | — | — | — |
| 1/100 | | — | — | — | 4454 | 5280 | 4.1 | — | — | — | — | — |
| 1/100 | | — | — | — | 4454 | 5280 | 2.2 | — | — | — | — | — |
| 1/200 | | — | — | — | 3983 | 4220 | Neg | 3880 | 5352 | 10.0 | Neg | Neg |
| 1/400 | | — | — | — | 3377 | 3719 | Neg | 3166 | 4161 | 4.8 | Neg | Neg |
| 1/500 | | 6238 | 9385 | 58.3 | — | — | — | — | — | — | — | — |
| 1/800 | | — | — | — | 3066 | 3351 | Neg | 3090 | 3607 | 2.5 | Neg | Neg |
| 1/1000 | | 6210 | 7836 | 43.7 | — | — | — | — | — | — | — | — |
| 1/1600 | | — | — | — | 2940 | Neg | Neg | 2924 | 3385 | Neg | Neg | Neg |
| 1/2000 | | 5275 | 6590 | 31.3 | — | — | — | — | — | — | — | ;13 |
| 1/3200 | | — | — | — | Neg | Neg | Neg | Neg | Neg | Neg | Neg | Neg |
| 1/4000 | | 4390 | 5346 | 21.1 | — | — | — | — | — | — | — | — |
| 1/6400 | | — | — | — | — | — | Neg | Neg | Neg | Neg | Neg | Neg |
| 1/8000 | | 3725 | 4288 | 10.6 | — | — | — | — | — | — | — | — |
| 1/12800 | | — | — | — | — | — | — | Neg | Neg | Neg | Neg | Neg |
| 1/16000 | | 3349 | 3774 | 5.7 | — | — | — | — | — | — | — | — |
| 1/32000 | | 3102 | 3459 | 3.0 | — | — | — | — | — | — | — | — |
| 1/64000 | | 2979 | Neg | Neg | — | — | — | — | — | — | — | — |
| N.C. Mean | | 2571 | 3010 | | 2571 | 3010 | | 2571 | 3010 | | 2571 | 3010 |
| S.D. | | ±90 | ±97 | | ±90 | ±97 | | ±90 | ±97 | | ±90 | ±97 |
| % C.V. | | 3.5 | 3.2 | | 3.5 | 3.2 | | 3.5 | 3.2 | | 3.5 | 3.2 |
| Cut Off | | 2931 | 3398 | | 2931 | 3398 | | 2931 | 3398 | | 2931 | 3398 |

Also, the 1:200 and greater dilutions of panel member number 326 (Code C) were determined as positive using both RI-Ad procedures, whereas Ausria II picked up only the 1:100 and lesser dilutions. For the same panel member, the 2 hour RI-Ad procedure gave positive results down to the 1:1600 dilution (a 16 fold greater sensitivity than Ausria II) and the overnight RI-Ad procedure gave positive results down to the 1:800 dilution (an 8 fold greater sensitivity than Ausria II). Further, for panel member number 336 (Code B), both RI-Ad procedures gave positive results down to the 1:1600 dilution, whereas positive results from the Ausria II procedure ceased at the 1:800 dilution (a 2 fold greater sensitivity over Ausria II). All of the dilutions tested for the negative panel member (number 317) were found to be negative.

EXAMPLE 2

Radioimmunoadsorbent Assay (RI-Ad ™) for Hepatitis B Surface Antigen in the form of Immune Complex with Antibody This example describes a procedure for detecting $HB_s$ antigen complexed with anti-$HB_s$, i.e., in the form of its immune complex. In this example the ability to detect $HB_s$ antigen in serum samples containing anti-$HB_s$, as well as the ability to detect $HB_s$ in the form of its immune complex in contrived samples, is demonstrated.

A. Preparation of Assay Columns

The columns were prepared as in the preceeding Example.

B. Assay Procedure

1. With the bottom cap in place and top cap removed, the phosphate buffer in the reservoir was poured from the column and replaced with 1 ml of 8M urea in 0.02M phosphate buffer (pH 6.8).

2. A 200 μl volume of the serum or plasma test sample, or a negative control sample, was added to the urea/buffer in the reservoir. The column was swirled to mix the sample and buffer/urea and was allowed to stand for 10 minutes before draining by removal of the bottom cap.

3. After draining, the procedure described in Part B of Example 1 was followed, beginning with step 3.

C. Detection of $HB_s$ antigen in serum with endogenous anti-$HB_s$

A negative control serum and a commercial (comm.) serum containing a low level of $HB_s$ antigen and anti-$HB_s$ were tested using the above modified RI-Ad procedure with a 2 hour/45° C. incubation, the Ausria II procedure mentioned in the previous Example, and the Ausab ® procedure (Abbott Laboratories, North Chicago, Illinois U.S.A.—radioimmunoassay for anti-$HB_s$). The results are given in Table 3.

Table 3

| Sample | modified RI-Ad, cpm | | Ausria II | Ausab |
|---|---|---|---|---|
| | Sample | Sample-CO* | P/N Ratio | RIA Units |
| neg. control | 3313 | Neg | Neg | Neg |
| comm. serum | 4574 | +321 | Neg | 477 |

*sample cpm bound minus cut-off value

The data indicates that the modified RI-Ad procedure is capable of detecting $HB_s$ antigen in the presence of endogenous anti-$HB_s$ (verified by Ausab results) whereas the Ausria II procedure could not.

In order to confirm the presence of $HB_s$ antigen in the commercial serum, a centrifugation experiment was performed. A sample of the commercial serum was equilibrated in glycine buffer (pH 2.0) and applied to a 5–20% weight to weight (w/w) sucrose gradient. The sample/gradient mixture was centrifuged at 36,000 revolutions per minute (rpm) for 3 hours. Fractions taken from the bottom part of the tube were found to be positive for $HB_s$ antigen by the Ausria II procedure. This corroborated the presence of $HB_s$ antigen in the commercial serum and clearly established that the $HB_s$ antigen, when separated from anti-$HB_s$ by centrifugation, could be detected by Ausria II whereas it had escaped detection in the commercial serum in which it was complexed with anti-$HB_s$.

D. Detection of $HB_s$ antigen in the form of its immune complex

A series of contrived test samples were prepared by adding increasing volumes of $HB_s$ antigen positive sera to a constant volume of high titer human anti-$HB_s$ sera. The final volumes were equalized with normal serum negative for both $HB_s$ antigen and anti-$HB_s$. After incubation for 20 hours, any precipitate which formed was removed by centrifugation and the supernatant saved as the contrived sample. Each contrived sample was tested using the modified RI-Ad procedure with a 2 hour/45° C. incubation, the Ausria II procedure, and the Ausab procedure. The results are given in Table 4. The "Ag/Ab Ratios" are the ratios of the volume of $HB_s$ antigen positive serum added to the volume of anti-$HB_s$ positive serum.

The modified RI-Ad procedure detected $HB_s$ antigen in the presence of anti-$HB_s$ to the lowest level of $HB_s$ antigen added (Ag/Ab Ratio = 0.2). At the point where anti-$HB_s$ was in excess (Ag/Ab Ratio $\leq$ 0.4), the Ausria II procedure failed to detect the presence of $HB_s$ antigen. The presence of anti-$HB_s$, on the other hand, was confirmed in the samples having Ag/Ab Ratios less than or equal to 1.0 by the Ausab procedure; however, the Ausab procedure itself failed to detect anti-$HB_s$ in the presence of excess $HB_s$ antigen (Ag/Ab Ratio $\geq$ 2.0).

Table 4

| Ag/Ab Ratio(v/v) | modified RI-Ad, cpm | | Ausria II P/N Ratio | Ausab RIA Units |
|---|---|---|---|---|
| | sample | sample-CO* | | |
| 4.0 | 34654 | +30755 | 107.4 | Neg |
| 3.0 | 34348 | +30449 | 127.9 | Neg |
| 2.0 | 29902 | +26003 | 146.9 | Neg |
| 1.0 | 9143 | +5272 | 11.3 | 16 |
| 0.4 | 5337 | +1438 | Neg | 54 × $10^2$ |
| 0.2 | 5707 | +1808 | Neg | 512 × $10^2$ |
| 0.0 | 3515 | Neg | Neg | 512 × $10^2$ |

*sample cpm bound minus cut-off value

EXAMPLE 3

Study of Adsorption Characteristics of Various Anion Exchange Materials for $HB_s$ Antigen The ability of the following anion exchange materials to adsorb $HB_s$ antigen as studied over the pH range 5.0 to 8.0:

(1) DEAE-cellulose (type DE-52 — Whatman Inc., Clifton, New Jersey U.S.A.)
(2) DEAE-Sephadex ® (Pharmacia Fine Chemicals, Piscataway, New Jersey U.S.A.)
(3) QAE-Sephadex ® (Pharmacia)
(4) DEAE-Biogel ® A (Bio-Rad Laboratories, Richmond, California U.S.A.)

Figure 3:
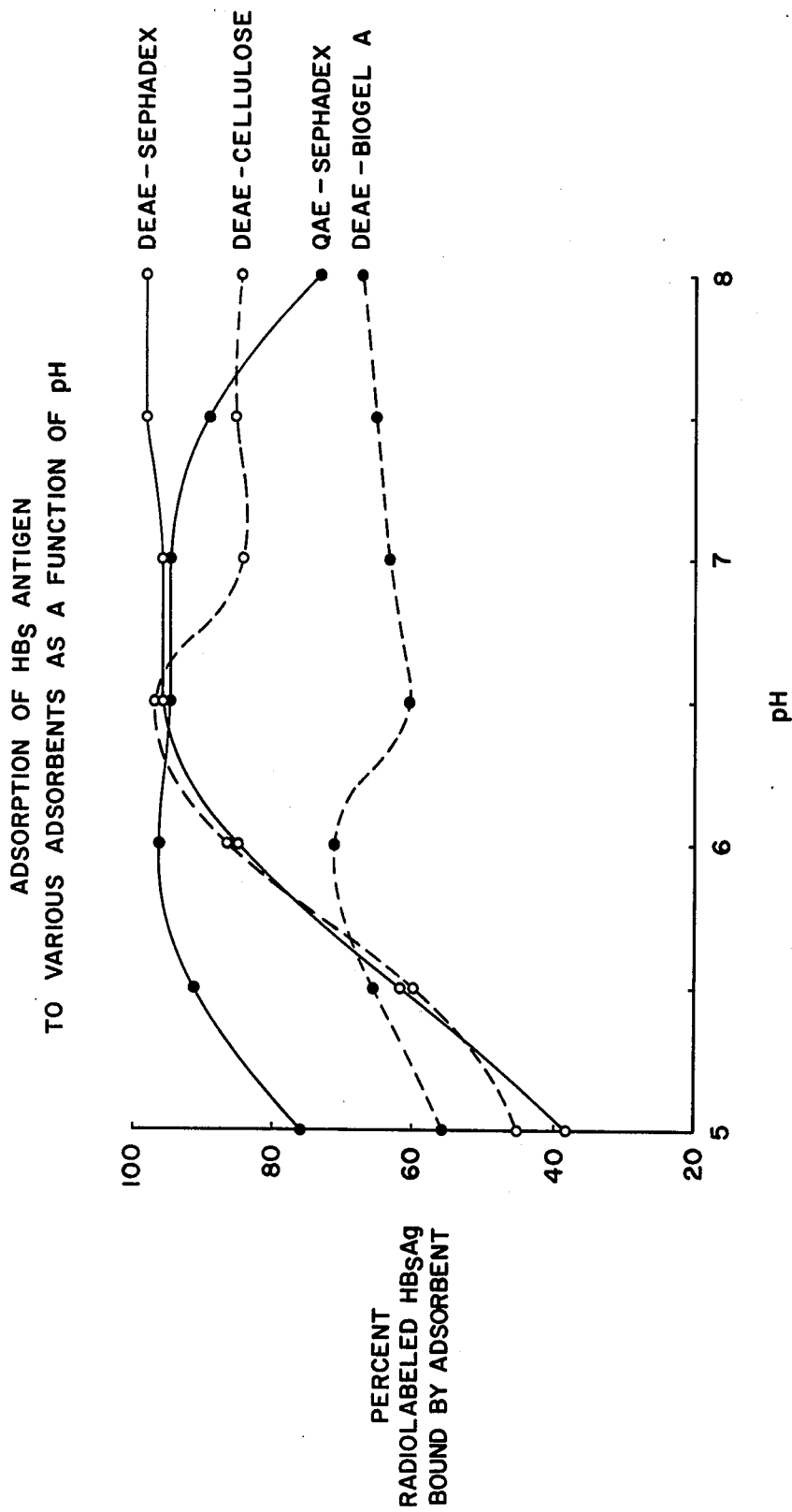
FIG. 3 is a graphical representation of the affinity of various adsorbents for $HB_s$ antigen under various conditions of pH.

A 200 μl volume of $^{125}$I-$HB_s$ antigen [25 nanograms per milliliter (ng/ml)] was added to each of a series of columns containing the various anion exchange materials at various known pH's. Each column was then washed with two 4.0 ml volumes of phosphate buffer at the corresponding pH. The columns were then counted in a gamma counter instrument. The results appear in graphical form in FIG. 3 of the drawings.

An optimum adsorption was observed at a pH of 6.0–6.5 for each of the resins examined. DEAE-cellulose, DEAE-Sephadex, and QAE-Sephadex showed similar maximum adsorption affinities for $HB_s$ antigen, while DEAE-Biogel A had a somewhat lesser affinity for the antigen. Overall, DEAE-cellulose was found to be the resin of preference in the column format because of its advantageous flow rate and minimum tendency to adsorb $^{125}$I-anti-HB$_s$.

EXAMPLE 4

Radioimmunoadsorbent Assay (RI-Ad ™) for Hepatitis B Surface Antigen (Alternative Procedure)

This example describes an alternative RI-Ad procedure for detecting HB$_s$ antigen wherein the wash step between sample application and addition of labeled anti-HB$_s$ is eliminated. The accuracy of this alternative RI-Ad procedure was assessed against BOB Reference Panel No. 3 (see Example 1).

Each panel member was tested by the RI-Ad 2 hour/45° C. procedure described in Example 1 (using a different batch of $^{125}$I-anti-HB$_s$) and by the same procedure without wash step 3. The results are given in Table 5. The cut-off value calculations for two procedures, i.e., "with wash" and "without wash", are given at the bottom of the table. The abbreviations are the same as those used in Example 1. A negative result, i.e., where cpm bound was less than the cut-off value, is indicated by a minus sign. The differences in cpm bound data produced in this Example using the wash step (Table 5) and that produced in Example 1 (Table 1) are due to the use of different batches of $^{125}$I-anti-HB$_s$.

Table 5

| Sample Number | BOB Code | cpm, bound with wash | cpm, bound without wash |
|---|---|---|---|
| 302 | D | 1865 (−) | 1784 (−) |
| 303 | N | 1898 (−) | 1673 (−) |
| 304 | C | 8010 | 3360 |
| 306 | A | 17136 | 6963 |
| 311 | N | 1734 (−) | 1760 (−) |
| 312 | A | 21200 | 6933 |
| 315 | (C) | 2133 (−) | 1644 (−) |
| 317 | N | 1934 (−) | 1734 (−) |
| 318 | C | 17647 | 8517 |
| 319 | B | 19705 | 6600 |
| 320 | B | 17745 | 4586 |
| 323 | C | 4210 | 2508 |
| 326 | C | 19427 | 8927 |
| 327 | B | 20541 | 6718 |
| 330 | A | 18369 | 6132 |
| 331 | N | 1876 (−) | 1821 (−) |
| 332 | C | 8821 | 3339 |
| 333 | C | 9502 | 4371 |
| 336 | B | 16319 | 5605 |
| 337 | C | 18811 | 11807 |
| 338 | C | 3631 | 2841 |
| 343 | (C) | 3650 | 2802 |
| 344 | C | 2894 | 2722 |
| 349 | D | 2146 (−) | 2482 |
| 350 | B | 16417 | 5251 |
| N.C. Mean | | 1814 | 1939 |
| S.D. | | ±86 | ±98 |
| % C.V. | | 4.7 | 5.05 |
| Cut-Off | | 2158 | 2331 |

This data indicates that elimination of the first wash step does not affect the ability of the RI-Ad procedure to detect as positive samples those BOB panel members having a code of A, B, or C.

EXAMPLE 5

Use of Hydrophobic Adsorbents in a Radioimmunoadsorbent (RI-Ad) Assay for Hepatitis B Surface Antigen In this example, a series of ω-amino alkyl-substituted agaroses were evaluated as adsorbents in the RI-Ad procedure described in Example 1. The test columns and assay procedure were as described in Example 1 except that the DEAE-cellulose adsorbent was replaced with various ω-amino alkyl-substituted agaroses and that in step 6 the adsorbent was washed with two consecutive additions of 2 ml of a mixture of tris-hydroxymethylaminomethane:hydrochloride buffer and 0.5M sodium chloride (pH 8.2). Two serum samples, one negative and one positive for HB$_s$ antigen, were tested using a series of columns, each containing a different one of the following materials having the general formula:

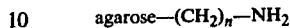

agarose—$(CH_2)_n$—$NH_2$ where n = 4 to 10, i.e., the number of carbons in the alkyl side chain.

| adsorbent | no. of side chain carbons | manufacturer's code no.* |
|---|---|---|
| ω-amino ethyl agarose | 2 | 62-080 |
| ω-amino butyl agarose | 4 | 62-081 |
| ω-amino hexyl agarose | 6 | 62-082 |
| ω-amino octyl agarose | 8 | 62-083 |
| ω-amino decyl agarose | 10 | 62-084 |

*Research Products Division of Miles Laboratories, Inc., Elkhart, Indiana U.S.A.

The results appear in Table 6.

Table 6

| no. of side chain carbons in adsorbent | cpm bound (positive sample) minus cpm bound (negative sample) |
|---|---|
| 2 | −93 |
| 4 | +70 |
| 6 | +358 |
| 8 | +1970 |
| 10 | +2117 |

The data indicates that ω-amino alkyl-substituted agaroses having alkyl side chains containing greater than 4 carbon atoms are useable adsorbents in the RI-Ad procedure for detecting HB$_s$ antigen.

EXAMPLE 6

Radioimmunoadsorbent Assay (RI-Ad) for Antibody to Hepatitis B Surface antigen

This example describes an assay procedure for the detection of anti-HB$_s$ using an anion exchange material pre-treated with a standardized amount of HB$_s$ antigen. The ability of the RI-Ad procedure to detect anti-HB$_s$ was assessed by comparision with the Ausab radioimmunoassay test kit marketed by Abbott Laboratories.

A. Preparation of Assay Columns

The columns were prepared as in Example 1.

B. Assay Procedure

1. The top cap was removed and the column placed in a drain rack.

2. A 200 μl volume of HB$_s$ antigen positive reference serum was added to the buffer in the reservoir above the DEAE-cellulose resin bed. The column was swirled to mix the sample and buffer and was then drained by removal of the bottom cap.

3. After draining, the resin bed was washed with two consecutive additions of 4 ml of 0.02M phosphate buffer (pH 6.8).

4. A 200 μl volume of the test sample, or a negative control sample, was then layered onto the top disc and allowed to flow into the resin bed.

5. The bottom cap was replaced and the column incubated for 2 hours at 45° C.

6. The bottom cap was removed and a 200 μl volume of $^{125}$I-anti-HB$_s$ was added to the top of the resin bed and allowed to flow into the resin bed. The bottom cap was then replaced and the column incubated an additional 2 hours at 45° C.

7. The bottom cap was removed and the resin bed was washed with two consecutive additions of 4 ml of 0.02M phosphate buffer (pH 6.8).

8. When the column had drained completely, the bottom cap was replaced, and the column counted in a gamma counting instrument.

C. Comparison with Ausab procedure

A series of serum samples positive for anti-$HB_s$ were tested by the above RI-Ad procedure and using Ausab kits, Abbott Laboratories, following the procedure given in the product insert. Anti-$HB_s$ titer was determined by both methods for each sample. Following the RI-Ad procedure, titer was defined as the greatest dilution of a sample resulting in inhibition of cpm bound greater than four standard deviations from a negative control mean (see Example 1). Following the Ausab procedure, titer was determined in RIA units according to the method given in the product insert. The results are given in Table 7.

Table 7

| Sample Number | RI-Ad Titer | Ausab Titer |
|---|---|---|
| 1 | $1.15 \times 10^3$ | $158 \times 10^3$ |
| 2 | $2.2 \times 10^3$ | $72 \times 10^3$ |
| 3 | $6.0 \times 10^2$ | $382 \times 10^3$ |
| 4 | $1.4 \times 10^3$ | $16 \times 10^4$ |
| 5 | $1.05 \times 10^3$ | $352 \times 10^3$ |
| 6 | $1.2 \times 10^3$ | $412 \times 10^3$ |
| 7 | $6.0 \times 10^2$ | $262 \times 10^3$ |
| 8 | $1.0 \times 10^2$ | $292 \times 10^3$ |
| 9 | $4.8 \times 10^2$ | $262 \times 10^3$ |
| 10 | $6.8 \times 10^2$ | $262 \times 10^3$ |
| 11 | $8.5 \times 10^2$ | $183 \times 10^3$ |
| 12 | $5.2 \times 10^2$ | $183 \times 10^3$ |
| 13 | $2.4 \times 10^3$ | $235 \times 10^3$ |
| 14 | $6.2 \times 10^2$ | $208 \times 10^3$ |
| 15 | $5.2 \times 10^2$ | $235 \times 10^3$ |
| 16 | $3.8 \times 10^2$ | $112 \times 10^3$ |

The data confirmed the ability of the RI-Ad procedure to detect the presence of anti-$HB_s$ comparable with the Ausab procedure.

What is claimed is:

1. A method for determining a specific binding substance in a liquid sample, comprising the steps of:
   (a) contacting said sample with (1) a specific binding partner of the substance to to determined, which binding partner is incorporated with a label and which labeled binding partner has a pI value different from that of said substance to be determined, and (2) a solid ion exchange adsorbent (i) of an anionic type when the pI value of said substance to be determined is less than that of said binding partner, or (ii) of a cationic type when the pI value of said substance to be determined is greater than that of said labeled binding partner; and
   (b) determining the amount of the label which either (i) becomes associated with the adsorbent by binding of the labeled binding partner with adsorbed substance to be determined or (ii) remains unassociated therefrom,
wherein step (a) is performed under conditions of pH between the pI value of the substance to be determined and that of said labeled binding partner.

2. A method as in claim 1 wherein step (a) is accomplished by (i) contacting the sample with the adsorbent and (ii) thereafter contacting the adsorbent with the labeled binding partner.

3. A method as in claim 1 wherein said adsorbent is contacted with the sample and the labeled binding partner substantially simultaneously.

4. A method as in claim 1 wherein step (b) is accomplished by (i) separating from the adsorbent substantially all of the labeled binding partner not associated therewith by binding with adsorbed substance to be determined, and (ii) measuring the amount of the label either associated with the adsorbent or separated therefrom.

5. A method as in claim 4 wherein said separation step is accomplished by washing the adsorbent whereby the amount of the label either associated with the washed adsorbent or contained in the washings can be measured.

6. A method as in claim 1 wherein said label is a radioactive material.

7. A method as in claim 1 wherein said substance to be determined is an antigen or a hapten and said specific binding partner thereof is an antibody.

8. A method as in claim 1 wherein said substance to be determined is hepatitis B surface antigen and said specific binding partner thereof is an antibody to hepatitis B surface antigen.

9. A method for determining a specific binding substance in a liquid sample, said substance to be determined having a pI value different from that of a specific binding partner thereof incorporated with a label, said method comprising the steps of:
   (a) contacting said liquid sample with a solid ion exchange material (i) of an anionic type when the pI value of said substance to be determined is less than that of said labeled binding partner, or (ii) of a cationic type when the pI value of said substance to be determined is greater than that of said labeled binding partner;
   (b) separating the ion exchange material and the unadsorbed portion of the liquid sample;
   (c) contacting the ion exchange material with said labeled binding partner; and
   (d) determining the amount of the label which either (i) becomes associated with the ion exchange material by binding of the labeled binding partner with adsorbed substance to be determined or (ii) remains unassociated therefrom;
wherein steps (a)-(c) are performed under conditions of pH between the pI value of said substance to be determined and that of said labeled binding partner.

10. A method as in claim 9 wherein step (b) is accomplished by washing the ion exchange material with a liquid having a pH between the pI value of the substance to be determined and that of the labeled binding partner.

11. A method as in claim 9 wherein step (d) is accomplished by (i) separating from the ion exchange material substantially all of the labeled binding partner not associated therewith by binding with adsorbed substance to be determined, and (ii) measuring the amount of the label either associated with the adsorbent or separated therefrom.

12. A method as in claim 11 wherein said separation step is accomplished by washing the ion exchange material with a liquid having a pH between the pI value of the substance to be determined and that of the labeled binding partner whereby the amount of the label either associated with the washed ion exchange material or contained in the washings can be measured.

13. A method as in claim 12 wherein said label is a radioactive material.

14. A method as in claim 13 wherein step (d) is accomplished by measuring the radioactivity of the washed ion exchange material or of the washings.

15. A method as in claim 9 wherein the difference between the pI value of the substance to be determined and that of the labeled binding partner is greater than 0.5.

16. A method as in claim 9 wherein the difference between the pI value of the substance to be determined and that of the labeled binding partner is greater than 2.0.

17. A method as in claim 9 wherein said substance to be determined is an antigen or a hapten and said specific binding partner thereof is an antibody.

18. A method as in claim 17 wherein said substance to be determined is hepatitis B surface antigen.

19. A method as in claim 9 wherein said substance to be determined is an antibody.

20. A method as in claim 19 wherein said substance to be determined is an antibody to hepatitis B surface antigen.

21. A method as in claim 9 wherein steps (a)–(d) are accomplished by:
  (a) introducing said sample to a column of said ion-exchange material in particulate form;
  (b) washing said ion exchange material in the column to remove substantially all of said substance to be determined not adsorbed to the ion exchange material;
  (c) introducing to said column a solution of said labeled binding partner; and
  (d) washing said ion exchange material in the column to remove substantially all of said labeled binding partner not associated with the ion exchange material by binding to adsorbed substance to be determined and measuring the label in the column or in the eluate from the last wash.

22. A method for detecting hepatitis B surface antigen in a liquid sample, comprising the steps of:
  (a) contacting said sample with a solid adsorbent of a type capable of nonspecifically binding with hepatitis B surface antigen;
  (b) contacting the adsorbent with an antibody to hepatitis B surface antigen, which antibody is incorporated with a label; and
  (c) determining the amount of the label which becomes associated with the adsorbent by binding of the labeled antibody with adsorbed hepatitis B surface antigen,
wherein steps (a) and (b) are performed under conditions favorable to binding between hepatitis B surface antigen and the adsorbent, and
either the adsorbent is of a type incapable of significantly binding with the labeled antibody under any conditions
or step (b) is performed under conditions unfavorable to significant binding between the labeled antibody and the adsorbent.

23. A method as in claim 22 wherein said adsorbent is a hydrophobic material.

24. A method as in claim 23 wherein said hydrophobic adsorbent is an ω-amino alkyl-substituted agarose having 4 to 10 carbon atoms in the alkyl group.

25. A method as in claim 22 wherein said adsorbent is an ion exchange material and wherein steps (a) and (b) are performed under conditions of pH between the pI value of hepatitis B surface antigen and that of the labeled antibody.

26. A method as in claim 25 wherein said labeled antibody has a pI value greater than that of hepatitis B surface antigen and wherein said ion exchange material is of an anionic type.

27. A method as in claim 26 wherein said anionic type exchange material is a diethylaminoethyl-substituted polymer.

28. A method as in claim 27 wherein the polymer is a polysaccharide.

29. A method as in claim 26 wherein said anionic type exchange material is a diethylaminoethyl-substituted cellulose.

30. A method as in claim 26 wherein the pI value of the labeled antibody is greater than 8.0 and wherein steps (a) and (b) are performed under conditions of pH between about 6.0 and 8.0.

31. A method as in claim 25 wherein said labeled antibody has a pI value less than that of hepatitis B surface antigen and wherein said ion exchange material is of a cationic type.

32. A method as in claim 22 which comprises the additional step between steps (a) and (b) of separating said adsorbent and the unadsorbed portion of the liquid sample.

33. A method as in claim 32 wherein said separation step is accomplished by washing the adsorbent under conditions favorable to binding between hepatitis B surface antigen and the adsorbent.

34. A method as in claim 22 wherein step (c) is accomplished by (i) separating from the adsorbent substantially all of the labeled antibody not associated with the adsorbent by binding with adsorbed hepatitis B surface antigen, and (ii) measuring the amount of the label either associated with the adsorbent or separated therefrom.

35. A method as in claim 34 wherein said separation step is accomplished by washing the adsorbent, whereby the amount of the label either associated with the washed adsorbent or contained in the washings can be measured.

36. A method as in claim 35 wherein said label is a radioactive material.

37. A method for detecting hepatitis B surface antigen in a sample of serum or plasma, comprising the steps of:
  (a) contacting said sample with a solid anion exchange material under conditions of pH between 5 and 8;
  (b) washing the anion exchange material with a liquid having a pH of between 5 and 8;
  (c) contacting the anion exchange material under conditions of pH between 5 and 8 with an antibody to hepatitis B surface antigen, which antibody is incorporated with a label and has a pI value greater than about 8; and
  (d) determining the amount of the label which either (i) becomes associated with the anion exchange material by binding of the labeled antibody with adsorbed hepatitis B surface antigen or (ii) remains unassociated therefrom.

38. A method as in claim 37 wherein step (d) is accomplished by washing the anion exchange material with a liquid having a pH between 5 and 8 and measuring the amount of the label either associated with the washed adsorbent or contained in the washings.

39. A method as in claim 38 wherein said label is a radioactive material.

40. A method as in claim 39 wherein said label is $^{125}I$.

41. A method for detecting hepatitis B surface antigen in a sample of serum or plasma, comprising the steps of:
(a) introducing said sample to a column of an anion exchange material in particulate form equilibrated in a liquid having a pH of between 5 and 8;
(b) passing through the column a liquid having a pH of between 5 and 8 to remove substantially all hepatitis B surface antigen not adsorbed to the anion exchange material;
(c) introducing to the anion exchange material a predetermined volume of a solution of radiolabeled antibody to hepatitis B surface antigen having a predetermined level of radioactivity;
(d) incubating the solution of radiolabeled antibody in contact with the anion exchange material for between ½ and 18 hours at a temperature of between 4° and 50° C.;
(e) passing through the column a liquid having a pH of between 5 and 8 to remove substantially all radiolabeled antibody not associated with the anion exchange material by binding to adsorbed hepatitis B surface antigen;
(f) measuring the radioactivity of the anion exchange material or of the eluate from the next previous step; and
(g) comparing the radioactivity measured in the next previous step to that measured following the same procedure using a liquid sample containing no significant amount of hepatitis B surface antigen in place of said serum or plasma sample.

42. A method as in claim 41 wherein said anion exchange material is a diethylaminoethyl-substituted polymer.

43. A method as in claim 42 wherein the polymer is a polysaccharide.

44. A method as in claim 41 wherein said anion exchange material is a diethylaminoethyl-substituted cellulose.

45. A method as in claim 41 wherein said liquids referred to in steps (a), (b), and (e) are pH buffers.

46. A method as in claim 45 wherein said pH buffers have a pH of between 6.5 and 7.5.

47. A method as in claim 46 wherein said pH buffers are phosphate buffers.

48. A method as in claim 41 wherein said antibody is radiolabeled with $^{125}I$.

49. A method for detecting hepatitis B surface antigen in the form of its immune complex with antibody in a liquid sample, comprising the steps of:
(a) combining said sample, an immunochemical-bond weakening agent, and a solid adsorbent of a type capable of and under conditions favorable to nonspecific binding with hepatitis B surface antigen;
(b) separating said bond weakening agent from the adsorbent; and
(c) determining the hepatitis B surface antigen bound to the adsorbent.

50. A method as in claim 49 wherein said adsorbent is an anion exchange material.

51. A method as in claim 50 wherein said bond weakening agent is a chaotropic agent.

52. A method as in claim 5 wherein said chaotropic agent is urea, guanidine, or thiocyanate.

53. A method as in claim 51 wherein said chaotropic agent is urea.

54. A method as in claim 53 wherein said anion exchange material is DEAE-cellulose.

55. A method as in claim 54 wherein urea is present at a concentration of between 2 and 8 molar.

56. A method as in claim 49 wherein step (c) is accomplished by contacting the adsorbent with antibody to hepatitis B surface antigen, which antibody is incorporated with a label, and determining the amount of label which either (i) becomes associated with the adsorbent or (ii) remains unadsorbed therefrom.

57. A method as in claim 56 wherein said label is a radioactive material.

58. A method for detecting an antibody to hepatitis B surface antigen in a liquid sample, comprising the steps of:
(a) providing a solid adsorbent having nonspecifically bound thereto hepatitis B surface antigen;
(b) contacting the adsorbent with said sample and with an antibody to hepatitis B antigen, which antibody is incorporated with a label; and
(c) determining the amount of the label which either (i) becomes associated with the adsorbent by binding of the labeled antibody to adsorbed hepatitis B surface antigen or (ii) remains unadsorbed therefrom,
wherein either the adsorbent is of a type incapable of significantly binding with the labeled antibody or step (b) is performed under conditions unfavorable to significant binding between the labeled antibody and the adsorbent.

59. A method as in claim 58 wherein said adsorbent is an anion exchange material.

60. A method as in claim 58 wherein step (c) is accomplished by (i) washing the adsorbent to separate therefrom substantially all of the labeled antibody not associated with the adsorbent by binding with adsorbed hepatitis B surface antigen, and (ii) measuring the amount of the label either associated with the washed adsorbent or contained in the washings.

61. A method as in claim 60 wherein said label is a radioactive material.

* * * * *